US00PP09483P

United States Patent [19]

Olesen et al.

[11] Patent Number: Plant 9,483

[45] Date of Patent: Mar. 26, 1996

[54] MINIATURE ROSE PLANT NAMED 'POULHAPPY'

[75] Inventors: Mogens N. Olesen; Pernille Olesen, both of Fredensborg, Denmark

[73] Assignee: Bear Creek Gardens, Inc., Medford, Oreg.

[21] Appl. No.: 410,359

[22] Filed: Mar. 24, 1995

[51] Int. Cl.[6] ..... A01H 5/00

[52] U.S. Cl. ..... Plt./10

[58] Field of Search ..... Plt./10

[56] References Cited

U.S. PATENT DOCUMENTS

P.P. 5,450 4/1985 Saville ..... Plt./10
P.P. 5,968 5/1987 Saville ..... Plt./10

*Primary Examiner*—Howard J. Locker
*Attorney, Agent, or Firm*—Klarquist Sparkman Campbell Leigh & Whinston

[57] ABSTRACT

A new rose variety of the miniature class having a compact, well-branched habit, good production of flowers in clusters, attractive red flowers and long shelf life as a potted rose.

1 Drawing Sheet

The present invention relates to a new and distinct variety of rose plant of the miniature class which was originated by me by crossing the variety POULvic, U.S. Plant Pat. No. 8,012, with an unnamed red flowered seedling, not patented.

The primary objective of this breeding was to produce a new rose variety having the habit of growth, clustering ability and shelf life of POULvic combined with the larger, bright red flowers of the unnamed seedling. The objective was substantially achieved, along with other desirable improvements, as evidenced by the following unique combination of characteristics that are outstanding in the new variety and that distinguish it from its parents, as well as from all other varieties of which I am aware:

1. Compact, well-branched habit.
2. Good production of flowers in clusters.
3. Attractive red flowers.
4. Good post-harvest shelf life as a potted rose.

Asexual reproduction of this new variety by softwood cuttings as performed at Wasco and Somis, Calif., as well as at Fredensborg, Denmark, shows that the foregoing and all other characteristics and distintions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—POULvic, U.S. Plant Pat. No. 8,012.
*Pollen parent.*—Unnamed seedling.

Classification:

*Botanical.*—Rosa hybrida.
*Commercial.*—Miniature.

FLOWER

Observations made from specimens grown in a greenhouse environment at Somis, Calif. and at Fredensborg, Denmark.

Blooming habit: Continuous.

Bud:

*Size.*—¾" long when the petals start to unfurl.

*Form.*—The bud form is pointed ovoid.

*Color.*—When sepals first divide, bud color is Red Group 46B. When half blown, the upper sides of the petals are Red Group 46B; and the lower sides of the petals are Red Group 46B.

*Sepals.*—Color: Green Group 138B. Surface texture: Covered in fine hairs. There are three heavily appendaged sepals. There are two unappendaged sepals with hairy edges.

*Receptacle.*—Color: Green Group 137C. Shape: Apple. Size: Small (3/16"×3/16"). Surface: Smooth.

*Peduncle.*—Length: Short (1"–1½"). Surface: Prickly. Color: Medium green. Strength: Stiff and erect.

Bloom:

*Size.*—Small. Average open size is 1½ inches.

*Borne.*—Singly and several together, in cluster of 3–7. If in clusters: Rounded to flat.

*Stems.*—Short and strong. Average length is about 6 to 8 inches.

*Form.*—When first open: High centered. Permanence: Flattens and outer petals curl back.

*Petalage.*—Number of petals under normal conditions: 25–30.

*Color.*—The upper side of the petals is Red Group 46B. The reverse side of the petals is Red Group 46B. The base of each petal has a small, White Group 155A half-moon at its point of attachment. The major color on the upper side is Red Group 46B.

*Variegations.*—Occasional white streak on guard petals and sometimes white on the tip of the center petals or petaloids.

*Discoloration.*—The general tonality at the end of the first day: No change. At the end of the third day: No change. By day 8, there is some fading to Red Group 46C.

*Fragrance.*—None.

Petals:

*Texture.*—Thick.

*Shape.*—Oval.

*Form.*—Tips slightly recurved.

*Arrangement.*—Imbricated, with few petaloids in the center.

*Persistence.*—Drop off cleanly.

*Lastingness.*—On the plant: Very long (12–14 days). As a cut flower: Very Long (12–14 days).

Reproductive parts:

*Anthers.*—Size: Medium. Quantity: Many. Color: Yellow. Arrangement: Regular around styles.

*Filaments.*—Color: Yellow.
*Pollen.*—Color: Lemon Yellow.
*Styles.*—Color: Greenish-White.
*Stigmas.*—Color: Yellow.

Form: Bush.

Growth: Vigorous, dwarf, upright, branching and compact; height at maturity in a 15 cm pot is 12–15 inches.

Foliage: Number of leaflets on normal mid-stem leaves: 5.
*Size.*—Small (3"×1½").
*Quantity.*—Abundant.
*Color.*—New foliage: Greyed-Orange Group 176A. Old foliage: Upper: Green Group 136B; Lower: Green Group 139C.

Leaflets:
*Shape.*—Pointed oval.
*Texture.*—Upper side: Glossy.
*Edge.*—Serrated.
*Serration.*—Single and small.
*Petiole rachis.*—Color: Green.
*Petiole underside.*—Smooth, with an occasional prickle.
*Stipules.*—Short and serrated.
*Disease resistance.*—Resistant to mildew under normal growing conditions at Somis, Calif. and Fredensborg, Denmark.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Short, straight to hooked slightly downward.
*Color when young.*—Red.

Small prickles:
*Quantity.*—On main stalks: None. On laterals: None.

I claim:

1. A new and distinct variety of rose plant of the miniature class, substantially as herein shown and described, characterized particularly as to novelty by the unique combination of its long shelf life as a flowering pot plant, its uniform, compact, well-branched habit of growth, its attractive red flowers and its clustering flower habit.

* * * * *

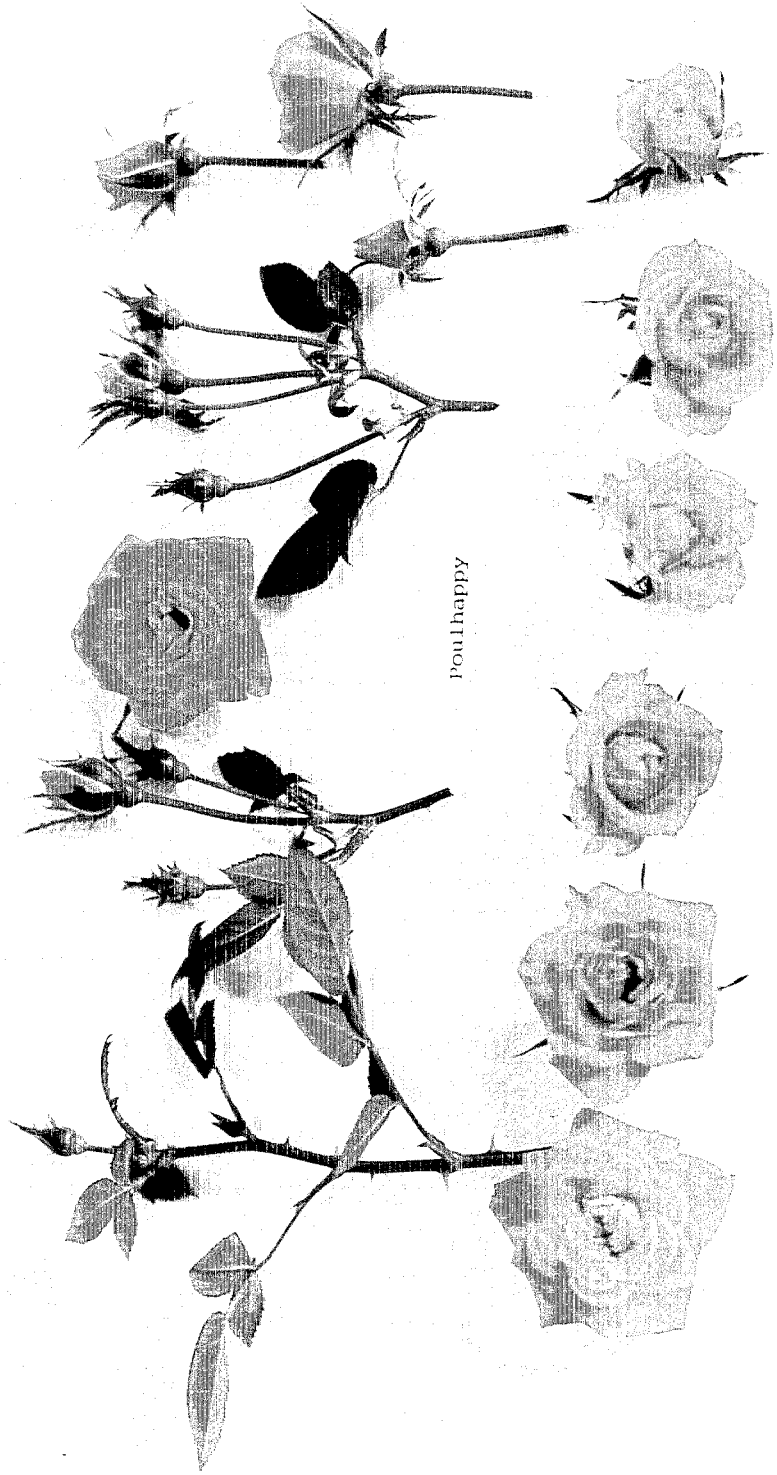
Pouthappy